United States Patent [19]

Dancer

[11] Patent Number: 5,483,333
[45] Date of Patent: Jan. 9, 1996

[54] METHOD AND APPARATUS FOR DETERMINING THE EXACT POSITION OF A TARGET USING A RECEIVING DEVICE COMPRISING A LINEAR ACTIVE PART FORMED FROM A VARIETY OF DISCRETE RADIATION-SENSITIVE ELEMENTS

[75] Inventor: Paul Dancer, 42100 Saint Ettenne, France

[73] Assignee: Technomed Medical Systems, Vaulx-En-Velin, France

[21] Appl. No.: 196,150

[22] PCT Filed: Aug. 18, 1992

[86] PCT No.: PCT/FR92/00798

§ 371 Date: Apr. 26, 1994

§ 102(e) Date: Apr. 26, 1994

[87] PCT Pub. No.: WO93/04380

PCT Pub. Date: Mar. 4, 1993

[30] Foreign Application Priority Data

Aug. 21, 1991 [FR] France .................................. 91 10498
Apr. 30, 1992 [FR] France .................................. 92 05413

[51] Int. Cl.$^6$ .............................. G01B 11/26; G06F 15/00
[52] U.S. Cl. .......................... 356/152.1; 364/413.14; 364/413.15; 364/413.26; 378/15; 378/19
[58] Field of Search .................... 356/152.1; 364/413.14, 364/413.15, 413.26; 378/15, 19

[56] References Cited

U.S. PATENT DOCUMENTS 4,041,315  8/1977  Hounsfield .............................. 250/360
4,764,944  8/1988  Finlayson ................................. 378/20
4,914,588  4/1990  Schittenhelm ...................... 364/413 H

FOREIGN PATENT DOCUMENTS

| 0260550 | 3/1988 | European Pat. Off. | A61B 17/22 |
| 0318106 | 5/1989 | European Pat. Off. | A61B 17/22 |
| 0449113A3 | 10/1991 | European Pat. Off. | H05G 1/26 |
| 87 13 524.8 | 2/1989 | Germany | G01T 1/29 |

*Primary Examiner*—Mark Hellner
*Attorney, Agent, or Firm*—Cohen, Pontani, Lieberman, Pavane

[57] ABSTRACT

Method and apparatus for determining the exact position of a target (C). The apparatus comprises a radiation source (22) emitting radiation forming an image of at least the target (C) capable of being received by a receiving device (30), said source (22) and said receiving device (30) being disposed on either side of the target (C), and the source (22) being in a known position in relation to a given point of reference (O) determined for example by a device (12) for treating the target (C). The apparatus is characterized in that the receiving device (30) comprises a header (32) having a linear active part formed from a variety of discrete radiation sensitive elements, whose positions in space are known, means (18) for displacing the radiation source between two different angular positions and means (40) for determining the position of the target (C) from at least two images obtained from two different angular positions of the radiation source. The invention provides means for limiting irradiation of a patient.

55 Claims, 9 Drawing Sheets

METHOD AND APPARATUS FOR DETERMINING THE EXACT POSITION OF A TARGET USING A RECEIVING DEVICE COMPRISING A LINEAR ACTIVE PART FORMED FROM A VARIETY OF DISCRETE RADIATION-SENSITIVE ELEMENTS

The present invention relates essentially to a method and an apparatus for determining the exact position of a target relative to a reference point of known coordinates with a receiving device comprising a linear active part formed from a variety of discrete radiation-sensitive elements.

The invention relates more particularly also to the use of the method and apparatus for determining the exact position of a target in an apparatus for the treatment of a target, preferably by pressure waves. According to a preferred embodiment, it is an apparatus for the treatment by pressure waves of a target selected from the group consisting of a lithiasis, for instance a renal or biliary lithiasis; of tissues, for instance benign or malignant tumors; bones, for instance a fracture or a bone zone to be treated, notably an osteoporosis zone.

Various methods and apparatuses are already known for determining the exact position of a target, comprising the use of a source of radiation emitting radiation capable of being received by a receiver device for this radiation, said source and said receiver device being disposed on opposite sides of said target (see EP-A-0,240,565 or EP-A-0,260,550).

Document Siemens DE-U-87/13,524=U.S. Pat. No. 4,914,588 describes an apparatus for forming an image by tomography requiring for constructing the image a rotating step around a rotation axis parallel to the patient's body to turn around it. The patient is usually displaced with a supporting table and this device requires a supplementary locating ultrasonic system.

Similarly, document EP-A-318,106 Philips=U.S. Pat. No. 4,967,735 describes an apparatus for the destruction of concretions comprising a fluoroscopic system combined with a system for detecting emitted photons, with the use of a diaphragm comprising a position of full opening and a position of reduced opening. The position, notably of the radiation source, appears to be fix, which generally implies an important irradiation of the patient.

It is further known, by document U.S. Pat. No. 4,764,944 (Finlayson) a method and a device for positioning a concretion located inside a patient's kidney using two convergent and penetrating radiation sources which intersect at focal point F2 consituting the external focus of an ellipsoid where are generated shock waves. Here, the initial position of the sources is not known but on the contrary must be very precise to intersect at the focal point. Besides, the technical solution proposed by Finlayson requires a calibrating step to determine the value of angle a between the coordinates in the observation plane and determine the angle between the observation plane and the horizontal. It is used in particular a rod terminated by a ball which is observed until the radiation observed by the fluoroscopes is centered on the intersecting point of each of the screens. This procedure is extremely complex and requires, in all the cases of use, two sources and two receiver devices, in particular fluoroscopes whose initial position must be well determined for each one of them by the second focus, which requires that the sources be linked permanently to the treatment device, here an ellipsoid. Besides, a calibrating is necessary with the help of the device comprising a ball to bring the ball image at the center of the fluoroscope screens.

Furthermore, it is also described, in document WO-A-91/07913, a method and device for determining the position of a target using a mask-forming device combined with a film sensitive to X-rays. This solution, which is safe and reliable, requires nevertheless a minimum time for developping the film which is not always compatible with the industrial and medical requirements.

Thus, a main object of the present invention is to solve the new technical problem consisting in providing a solution enabling to determine the exact position of a target in a relatively short time while being of a great reliability and reproducibility.

A further main object of the present invention is to solve the new technical problem consisting in the provision of a solution enabling to determine the exact position of a target without requiring any displacement of the device for treating the patient and/or of the patient.

Another main object of the present invention is to solve a new technical problem consisting in providing a method and an apparatus for determining the exact position of a target without requiring to bring this target in a determined position with respect to the treatment device and/or without requiring to bring it into a determined position with regard to the radiation receiver device.

Another main object of the present invention is to solve the new technical problem consisting in the provision of a method and an apparatus for determining the exact position of a target using a radiation of a substantially uniform intensity when received by the receiver device, to improve the quality of the obtained image.

A further main object of the present invention is to solve the new technical problem consisting in the provision of a method and apparatus more simple, with an easy setting and maintenance, reducing the exposure of the patient to the radiations, what is particularly important in the case of X rays and enabling to occupy a minimum space during storage and transportation.

Another object of the present invention is to solve the new technical problems specified above with a minimum of manipulations, notably a mimum of steps, or of pictures or of displacements, thus limiting the dose of exposure to the radiation emitted with regard to the by the radiation source, which is particularly important when the radiation source emits X rays.

A further object of the present invention is to solve the new technical problems specified above in a manner such that the retained solution permits to use the method and apparatus of the invention in an apparatus for the treatment of a target, preferably by pressure waves, more preferably this target being selected from the group consisting of a lithiasis, for instance a renal or biliary one; tissues, for instance benign or malignant tumors, and bones, for instance a bone zone, such as a fracture or an osteoporosis zone.

For the first time, the present invention renders possible to solve the technical problems specified above simultaneously, particularly simply, cheaply and in a manner that is usable on an industrial and medical scale.

Thus, in a first aspect, the present invention provides a method for determining the exact position of a target (C) relative to a reference point (O) determined, for example, by a device for treating the target (C), comprising using an emission device comprising a radiation source emitting an image formation radiation for forming an image at least of the target (C) and capable of being received by a receiver device for receiving said radiation, said source and said receiver device being disposed on opposite sides of said target (C), said source being of known position relative to said reference point (O), and determining the position of said target (C) from at least one image of said target (C), wherein said receiver device is provided in the form of a bar comprising a linear active part formed from a variety of multiplicity of discrete radiation-sensitive elements ($e_1$ to $e_n$) whose positions in space are known, and displacing simultaneously said radiation source and said receiver device, either in translation, or in rotation according to a direction non perpendicular to the line defined by said linear active part.

According to another advantageous embodiment, said radiation source and said receiver device are displaced in translation simultaneously along a distance permitting to emit a radiation covering at least the target zone (C); said displacement in translation being advantageously performed for at least two different orientations or inclinations of said associated radiation source and receiver device.

According to an other advantageous embodiment, said radiation source and said receiver device are simultaneously rotated according to a rotation axis substantially parallel to said line defined by said linear active part.

According to a further embodiment of the invention, the radiation source and the receiver source are mounted onto a single common support device, preferably in the form of a C arm having one end located above said target and another end located below said target. Advantageously, said common support device is mounted in rotation around a rotation axis advantageously located substantially perpendicularly to said longitudinal axis of said apparatus which is usually defined by the longitudinal axis of a so-called working table, supporting a patient laying on said table according to the same longitudinal axis; said rotation axis being preferably mounted parallely to said sensitive active surface of said receiver device.

According to a particular variant implementation, said common support device is displaced in translation according to a direction substantially perpendicular to the rotation axis which is itself mounted parallel to the sensitive active surface of said receiver device.

According to a further particular variant implementation, said common support device is displaced in translation along a distance permitting to emit a radiation covering at least the target zone. Said translation displacement being performed for at least two distinct orientations or inclinations of said common support device which are obtained by an easy rotation around said rotation axis.

According to a particular embodiment, said common support device is mounted in rotation on a support clement forming a part of a carriage mounted displaceable in translation on at least one or preferably two guiding rails for guiding in translation, rigidly locked with the frame of the apparatus.

According to a further embodiment, the source is an X-ray source and the receiver device comprises discrete elements sensitive to X radiation.

According to a further invention embodiment, said source is an X-ray source and said radiation device comprises at least a fluoroscopic screen sensitive to X rays and discrete elements sensitive to the fluoroscopic radiation of said screen, for instance discrete elements sensitive to light photons.

According to a further embodiment, the discrete elements comprise components in the solid state which are sensitive to X rays, for instance semiconductor elements.

According to a further embodiment, said method performs the displacement of the receiver device according to a predetermined known displacement speed, which permits to determine the position of said receiver device at a given instant.

According to a further embodiment, the method is determining which is the discrete element which has received the image of the target (C), for each of said two images resulting from said two distinct angular positions of the radiation source and from the knowledge of the exact position of said discrete elements having receiving said two images of target (C) resulting from the two positions of the radiation source, and determining the exact position in space of said target.

According to a further embodiment, said method provides a monitor screen on which is projected at least an image of the zone of said target (C) obtained when displacing said receiver device, as well as pointing means for pointing the position of said target (C) on the screen and calculating means for calculating the position of said target (C) with said pointing means, for each image.

According to a further embodiment, said method provides a collimation device enabling to limit in space the radiation zone, which permits to limit the irradiation of the patient; which is preferably displaced simultaneously with the radiation source and the receiver device.

According to a further embodiment, said method provides that the receiver device comprises said linear part formed from a variety or multiplicity of discrete radiation-sensitive elements whose positions in space are known, thereby defining a general plane for receiving said radiation, provides that the radiation source emits said radiation initially in a direction substantially perpendicular to said receiving plane, said radiation initially perpendicular to said plane being reflected by a reflecting device optionally re-emitting said radiation, in a direction parallel to said receiving plane, and providing a collimation device comprising a collimation slot parallel to said receiving plane and limiting the radiation zone substantially to the substantially linear size of said active part of said receiver device. Preferably, the radiation source is an X-ray tube whose axis is advantageously located substantially perpendicularly to said direction of said receiving plane. Due to the invention, the variations of intensity of the radiation reaching the sensitive zone of said receiver device are minimized because it was observed that the radiation is more uniform when the source has its axis located substantially perpendicularly to said direction of the receiving plane, after having been reflected into this plane by a reflecting device generally named cathode.

Due to the fact that the radiation source and receiver device are mechanically linked or locked by being mounted on a common support device, the conception of the structure of the device and of the performing of the locating method is simplified, the setting and the maintenance are easy. The exposure of the patient to the radiations is reduced, which is particularly of interest in the case of X rays. Besides, by the mounting of the common support device in rotation and also in translation, it is possible to fully free the common support along the apparatus which limits the overall dimensions when storing or transporting, without dismounting. The manufacture of the radiation device and of the receiver device may also be preset.

According to a second aspect, the present invention provides a device for determining the exact position of a target (C) relative to a reference point (O) determined for instance by a treatment device of said target (C), comprising an emitting device comprising a radiation source emitting an image-forming radiation at least of said target (C) capable of being received by a receiver device for said radiation, said source and said receiver device being mounted on opposite sides of said target (C), said source being of a known position relative to said reference point (O); and means for determining the position of said target (C) from at least one image of said target, wherein said receiver device is under the form of a bar comprising a linear active surface formed from a variety or multiplicity of aligned discrete elements ($e_1$ to $e_n$) sensitive to said radiations whose positions in space are known; and displacing means for displacing simultaneously said radiation source and said receiver device, in particular according to a predetermined known displacing speed, as well as calculating means for calculating the position of said receiver device at a given instant from the time of displacement and the known displacing speed.

According to an independently patentable embodiment, said radiation source and said receiver device are mounted onto a common support device, preferably having a C-arm shape whose ends are disposed on opposite sides of the target.

According to a particular embodiment, the emitting device comprises displacing means for displacing the radiation source between two distinct angular positions and determining means for determining the position of target (C) from at least two images obtained from said two distinct angular positions of said source.

According to a further embodiment, said source is an X ray source and the receiver device comprises discrete elements sensitive to said X rays.

According to a further variant implementation of the invention, said source is an X ray source and the receiver device comprises at least a fluoroscopic screen sensitive to X rays and discrete elements sensitive to said fluoroscopic radiation from said screen, for instance discrete elements sensitive to light photons.

According to a further embodiment, said discrete elements comprise components under the solid state and sensitive to X rays, for instance semiconductor elements.

According to a further embodiment, said determining means for determining the position of the receiver device at a given instant are foreseen to determine which is the exact position of the discrete element which has received the image of target (C) and the instant or time at which said element received said image, for each one of the two images resulting from said two distinct angular positions of said radiation source, as well as to determine the scan position in space of target (C) from the knowledge of the exact position of said two discrete elements having received said two images of target (C) resulting from said two positions of the radiation source.

According to a particular variant implementation, a monitor screen is foreseen on which at least an image of the zone of target (C) obtained when displacing said receiver device is projected, as well as pointing means for pointing the position of target (C) on the screen and calculating means for calculating the position of target (C) with said pointing means, for each image.

According to a further embodiment, a collimation device is foreseen, enabling to limit in space the radiation zone, thereby limiting the irradiation of the patient.

According to a further embodiment, the radiation source emits the radiation in an initial direction substantially perpendicular to a receiving plane defined by the linear active part and said rotation axis, a reflecting device being foreseen to perform a reflection of said radiation into the receiving plane, as well as an optional collimation device comprising a slot located parallely to the receiving plane and in a direction perpendicular to the initial direction of said radiation.

According to a third aspect, the present invention covers still the use of the method and/or of the device in an apparatus for the treatment of a target, preferably by pressure waves. This apparatus for treatment is in particular an apparatus for the treatment of a target selected from the group consisting of a lithiasis, for instance a renal or biliary lithiasis; of tissues, for instance benign or malignant tumors; of bones, for instance a fracture or an osteoporosis zone. A preferred apparatus for the treatment is characterized in that it comprises a truncated ellipsoidal reflector filled with a coupling liquid comprising an inner focus immersed in said liquid and an external focus to be put in coincidence with the target to be treated, as well as at least two electrodes located symmetrically on opposite sides of said internal focus to generate said pressure waves at said internal focus through electrical discharge in said coupling liquid.

It will be understood that the invention solves the new technical problems previously set forth, to reach the above-mentioned highly important technical advantages, as well as those which will appear clearly to one skilled in the art from the following description of the invention which is made with reference to a presently preferred embodiment of the invention which is given purely by way of example, the scope of the invention being naturally not limited in any way to these specific examples. In the drawings.

Figure 7:
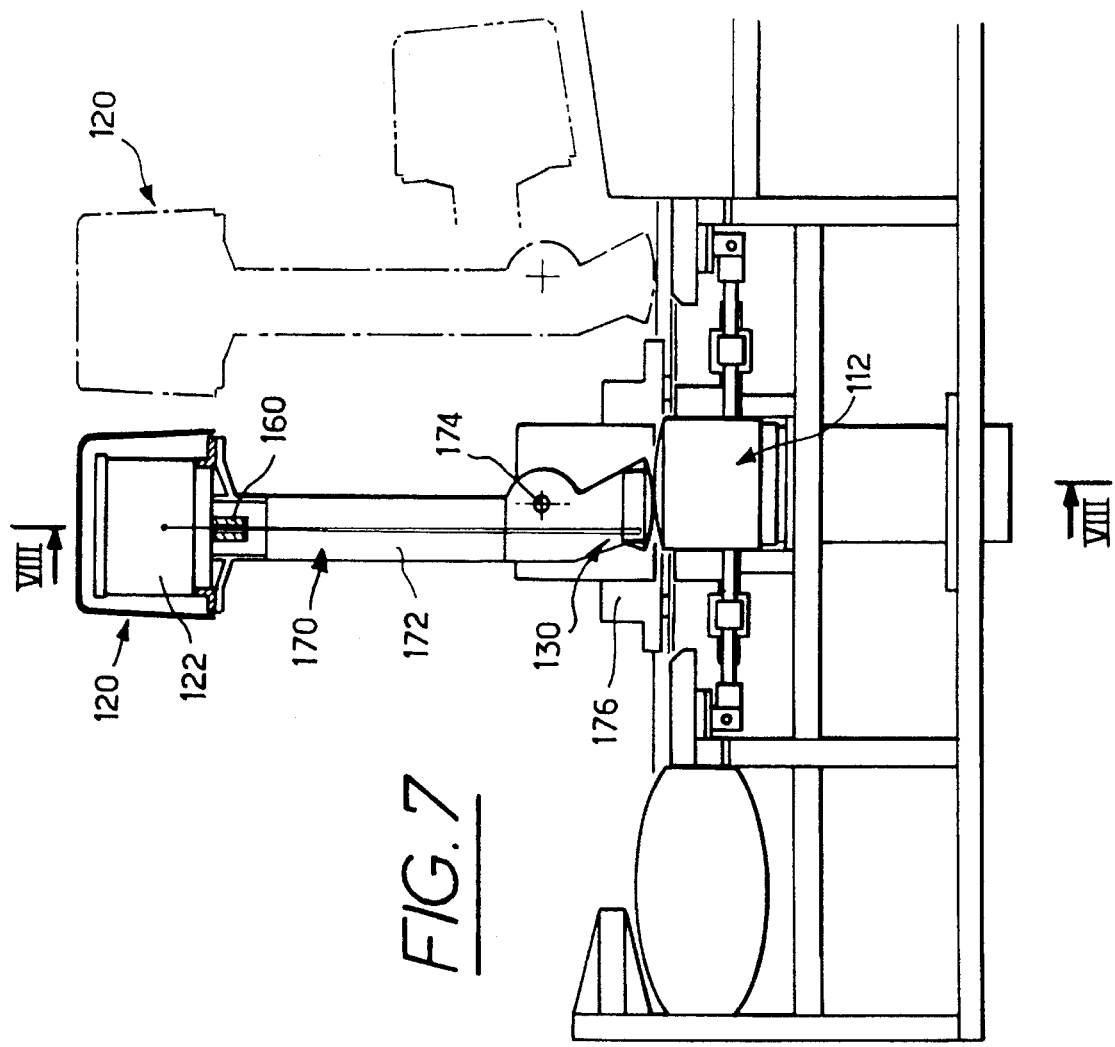
FIG. 7 represents a partial cross-section view according to the longitudinal axis of said apparatus of FIG. 6, or again according to the cross-section line VII—VII of FIG. 8.
Figure 8:
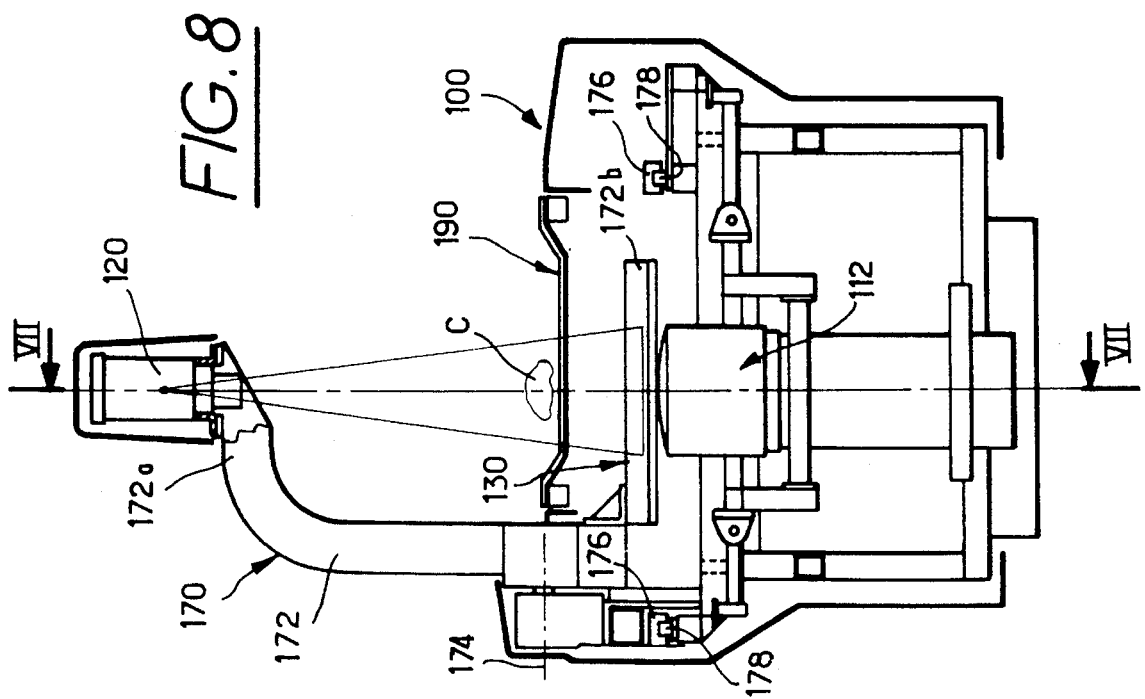
Figure 9:
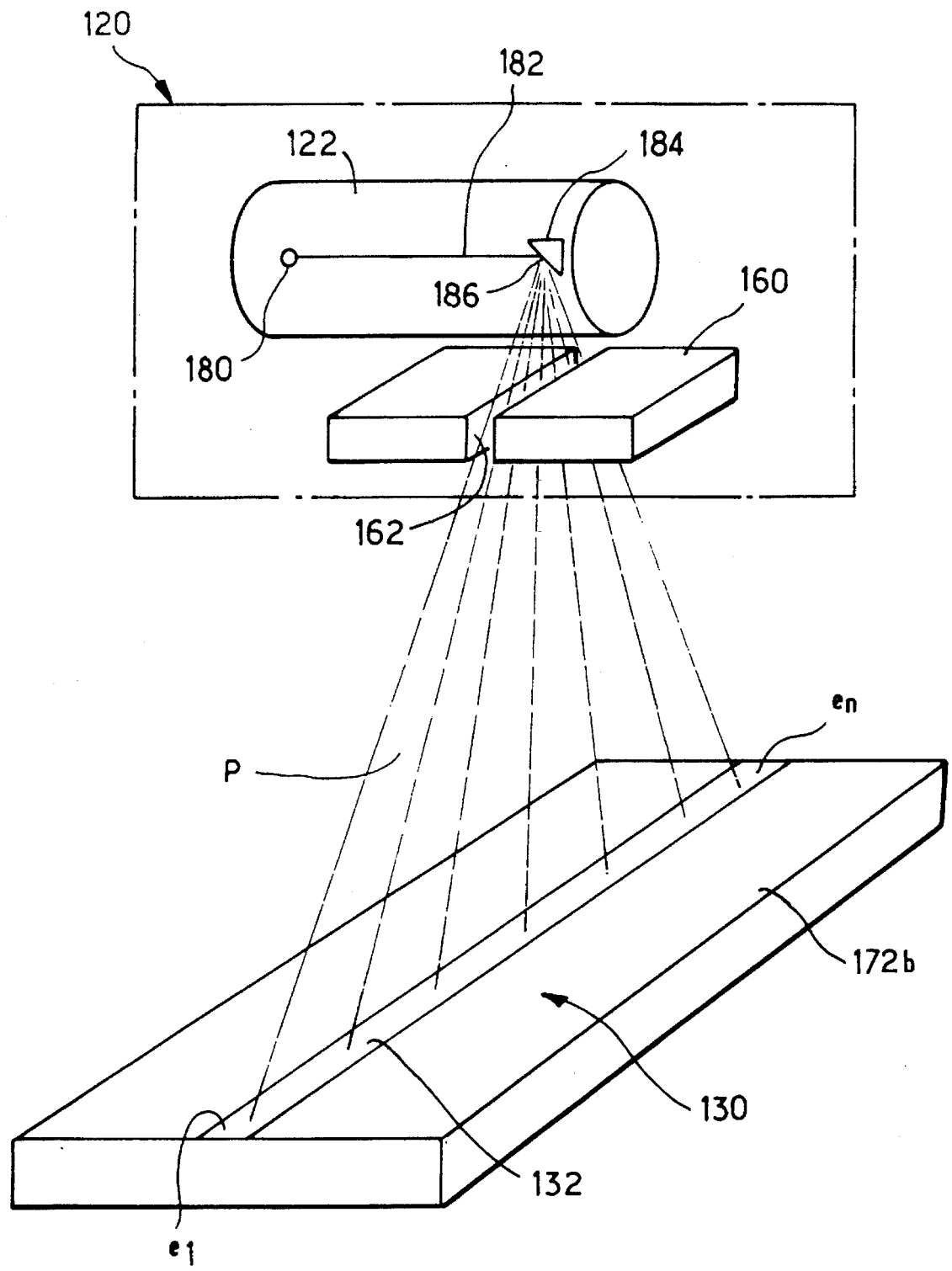

FIG. 8 represents a partial cross-section view according to the cross-section line VIII—VIII of FIG. 7; and FIG. 9 represents diagrammatically and on a larger scale the initial direction of the radiation, for instance a X ray beam, with regard to the collimation device and to the receiving plane of the receiver device comprising a linear active surface formed from a plurality of aligned radiation receiving elements.

Figure 1:
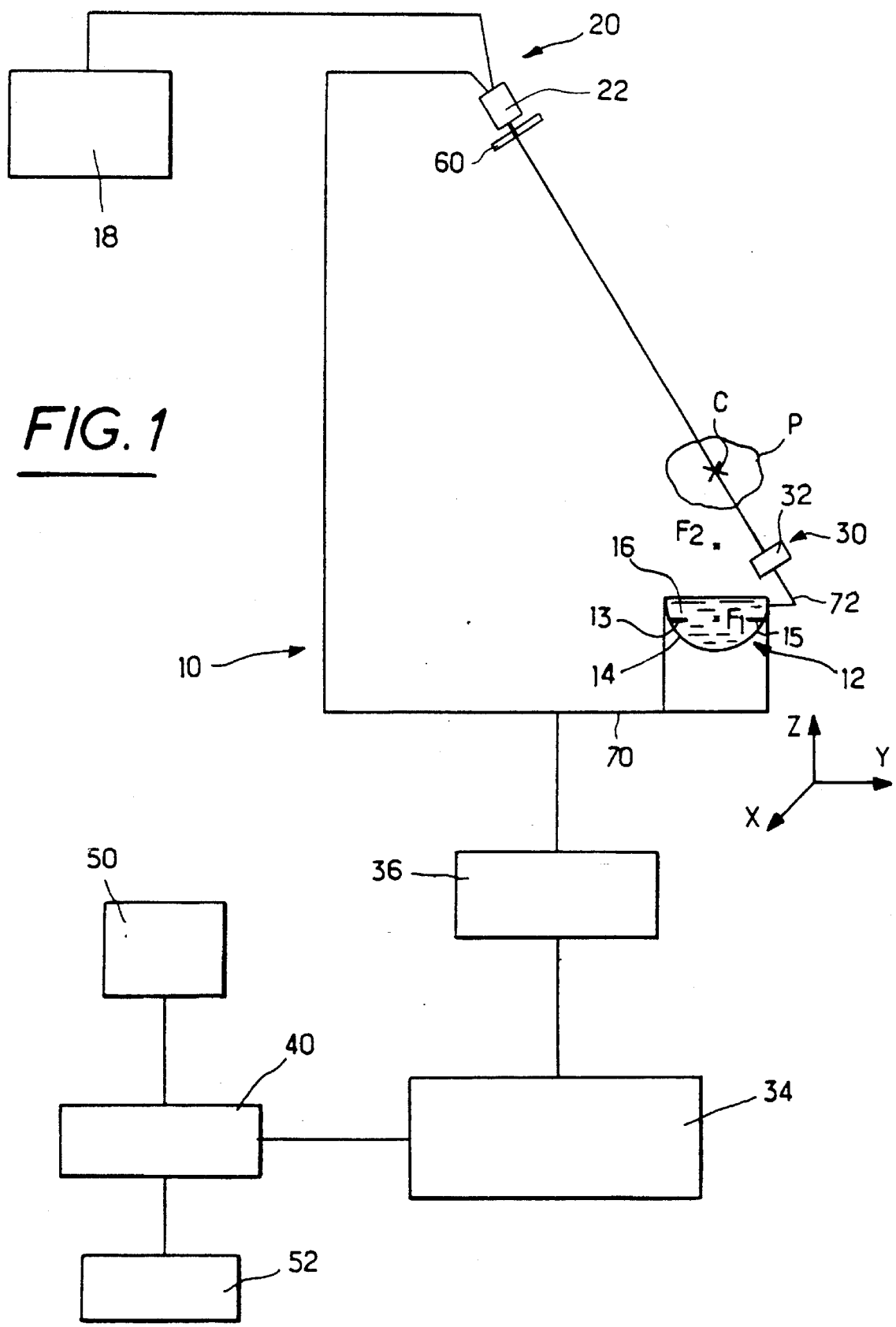
FIG. 1 is a diagrammatic principle view of an apparatus for the treatment of the target (C) to be treated, for example, here, a renal lithiasis inside the kidney of a patient.

With reference to FIGS. 1 to 5, and more particularly to FIG. 1, an apparatus according to the present invention for the treatment is represented by an overall reference number 10. This apparatus for treatment is preferably an apparatus for treatment emitting pressure waves, still preferably pressure waves focused on a focal point F 2, aimed to be put into coincidence with the target C to be treated. Thus, this apparatus comprises a pressure waves generating device 12. According to a preferred embodiment, as shown, this pressure waves generating device 12 comprises a truncated ellipsoidal reflector 14 filled with a liquid 16, which is well known to one skilled in the art and for instance described in US RIEBER U.S. Pat. No. 2,559,227 or as well in prior Applicant's documents, such as U.S. Pat. Nos. 4,730,614; 4,866,330; 4,915,094; 4,962,753 to which one skilled in the art may refer. This truncated ellipsoidal reflector 14 comprises an inner focus $F_1$ and an external focus $F_2$ aimed to be put into coincidence with the target C to be treated. This reflector 14 is provided with at least two electrodes 13, 15 disposed symmetrically relative to the internal focus $F_1$ and are generating through an electrical discharge, with the help of a high voltage generator, pressure waves at said focus $F_1$, which are focused onto said external focus $F_2$ by being transmitted by said coupling liquid 16, as it is well known to one skilled in the art. Device 12 is usually mounted displaceable in space in three directions X, Y, Z, due to the monitoring means 34, for example with motors 36.

The invention apparatus 10 comprises an emitting device 20 comprising a radiation source 22 emitting an image forming radiation at least of target C capable of being received by a receiver device 30 of said radiation point. Source 22 and receiver device 30 are located on opposite sides of said target C. Besides, source 22 is in a known position relative to reference point O. In the case of the preferred embodiment, reference point O is constituted by the external focus F2 of said truncated ellipsoidal reflector 14.

Figure 2:
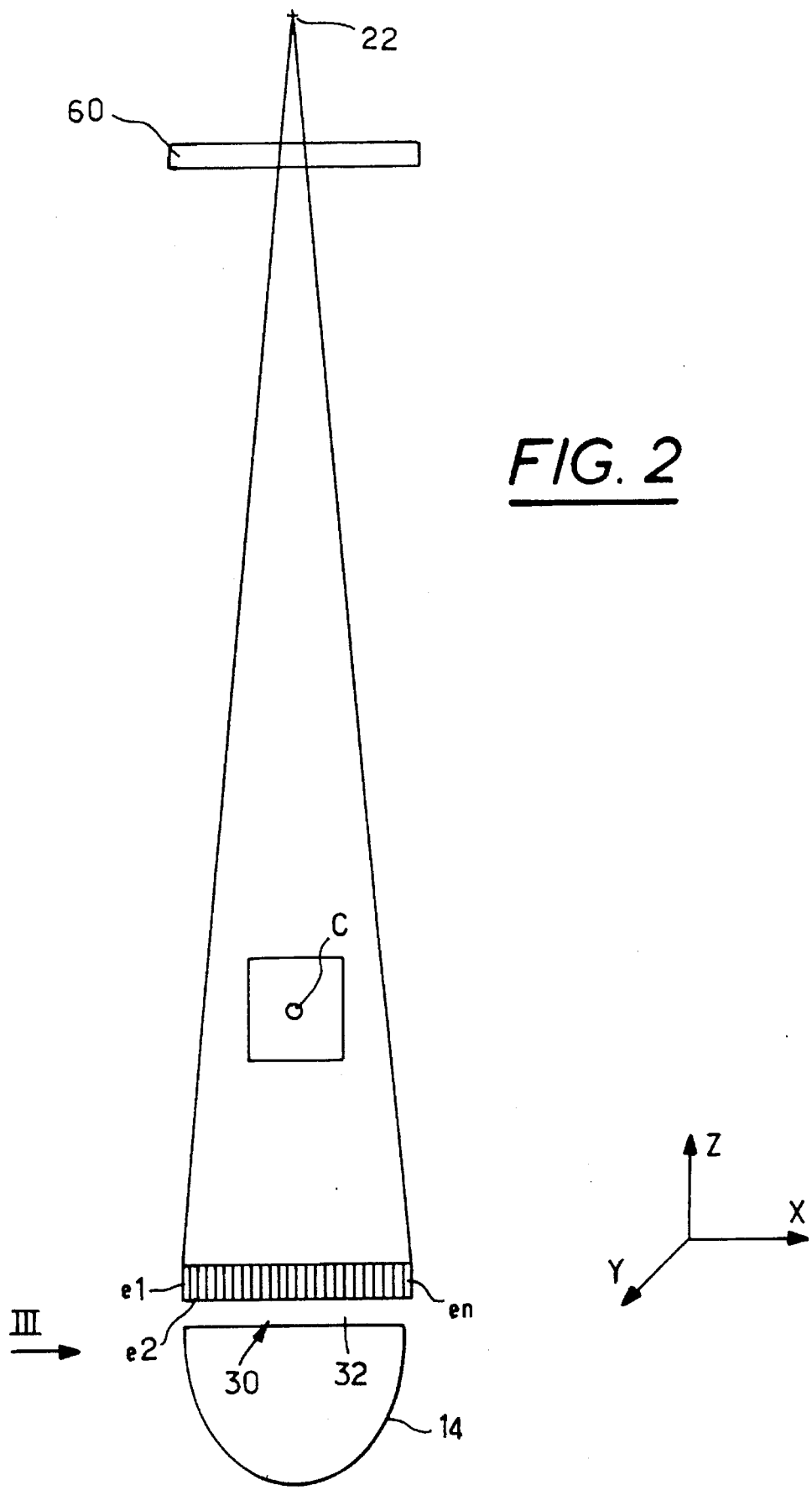
FIG. 2 represents a diagrammatic view according to arrow II of FIG. 3.
Figure 3:
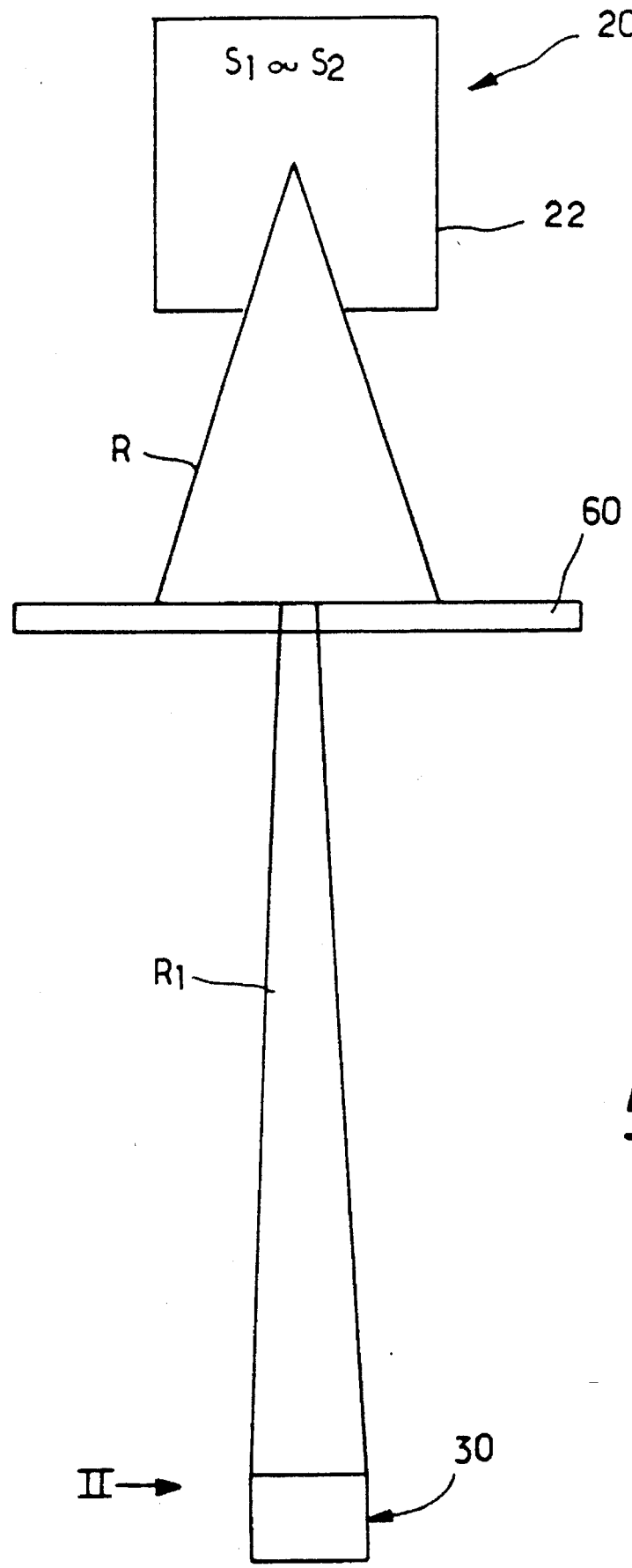
FIG. 3 represents a diagrammatic view according to arrow III of FIG. 2 showing the reduction of the radiation volume due to the use of a collimation device.
Figure 5:
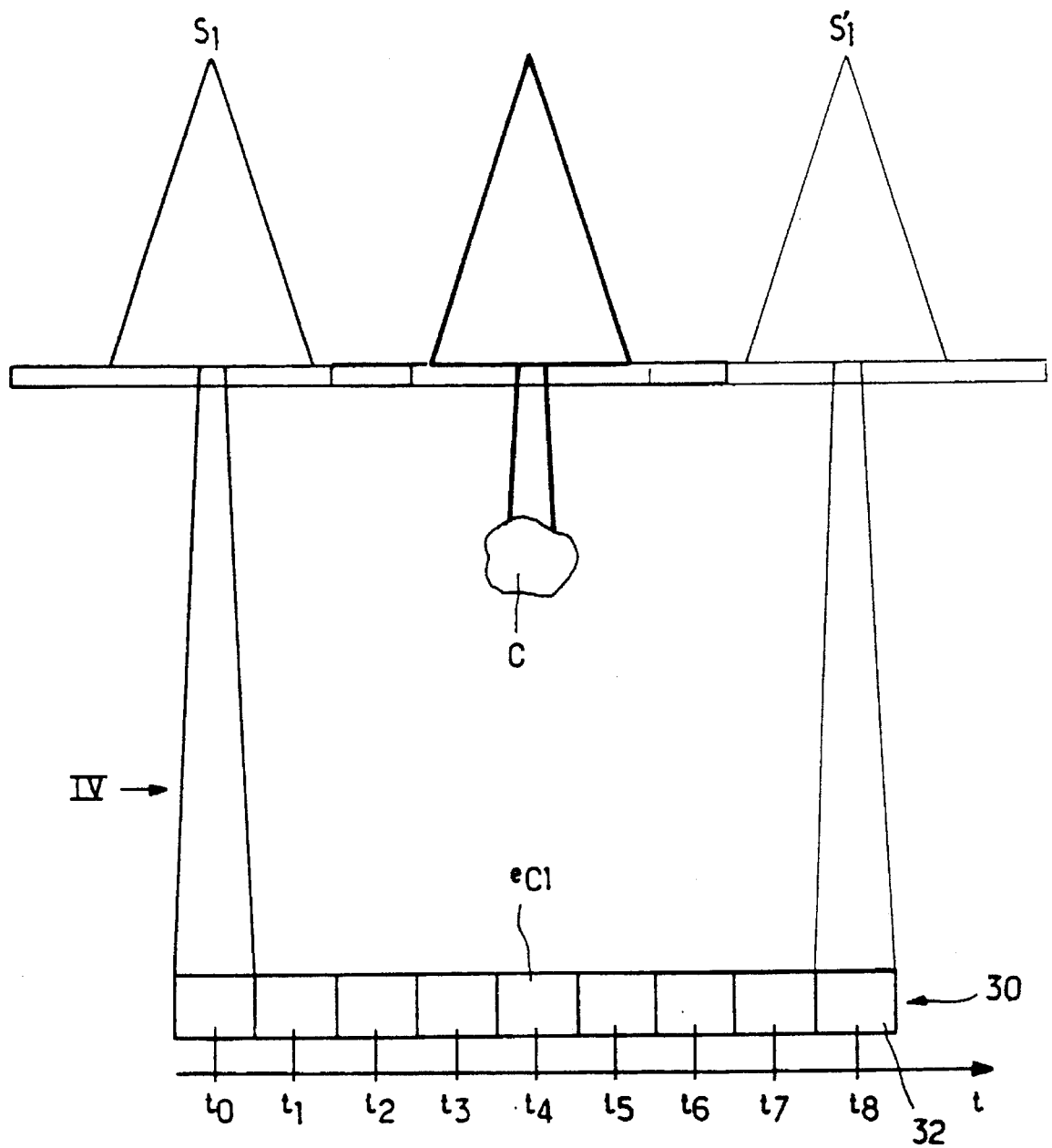
FIG. 5 represents diagrammatically the receptive positions during the time enabling to observe the position for which the radiation reaches target C.

According to the present invention, the apparatus is characterized in that the receiver device 30 comprises a bar 32 comprising a linear active part formed from a multiplicity or variety of aligned discrete elements $e_1, e_2, \ldots, e_n$, sensitive to said radiation, which positions in space are known, which are particularly well seen on FIGS. 2 and 5.

On the other hand, said apparatus also comprises determining means 40 for determining the position of target C from at least one and preferably at least two images obtained from said distinct angular positions $S_1, S_2$ of source 22.

The apparatus also comprises displacing means (not shown) for displacing said source 22, which are well known to one skilled in the art.

According to a particular feature, said receiver device 30 is realized under the form of a bar 32, displacing means 34 for displacing said bar 32 being foreseen to displace said bar 32 so as to cover at least the entirety of the zone of target C.

According to a variant embodiment, source 22 is a X-ray source and receiver device 30 comprises discrete elements, referenced $e_1, e_2, \ldots e_n$ on FIG. 2, which are sensitive to X rays, preferably disposed parallel and aligned to define a receiving linear active surface.

According to a further variant embodiment of the invention, source 22 is a X-ray source and receiver device 30 comprises at least one fluoroscopic screen sensitive to X rays and discrete elements, reference $e_1, e_2, \ldots, e_n$, FIG. 2, sensitive to said fluoroscopic radiation from said screen, for example discrete elements sensitive to light photons.

According to another embodiment, the discrete elements $e_1$ to $e_n$ comprise components under solid state sensitive to X radiation, for example semiconductors elements.

According to another further embodiment of the invention, displacing means 34 for displacing said receiver device 30 are foreseen, capable of performing the displacement of said receiver device 30 according to a predetermined known displacing speed, as well as calculating means 40, comprising for example a calculator, computer or microcomputer, enabling to calculate the position of the receiver device 30 at a given moment, for instance from the known displacement time and the known displacement speed, as it is well understood from the consideration of FIG. 4 which shows the movement of displacement of bar 32 in function of time during displacement. Positions of bar 32 are represented $t_0$, $t_1$, $t_2$ up to $t_8$ for example.

Figure 4A:
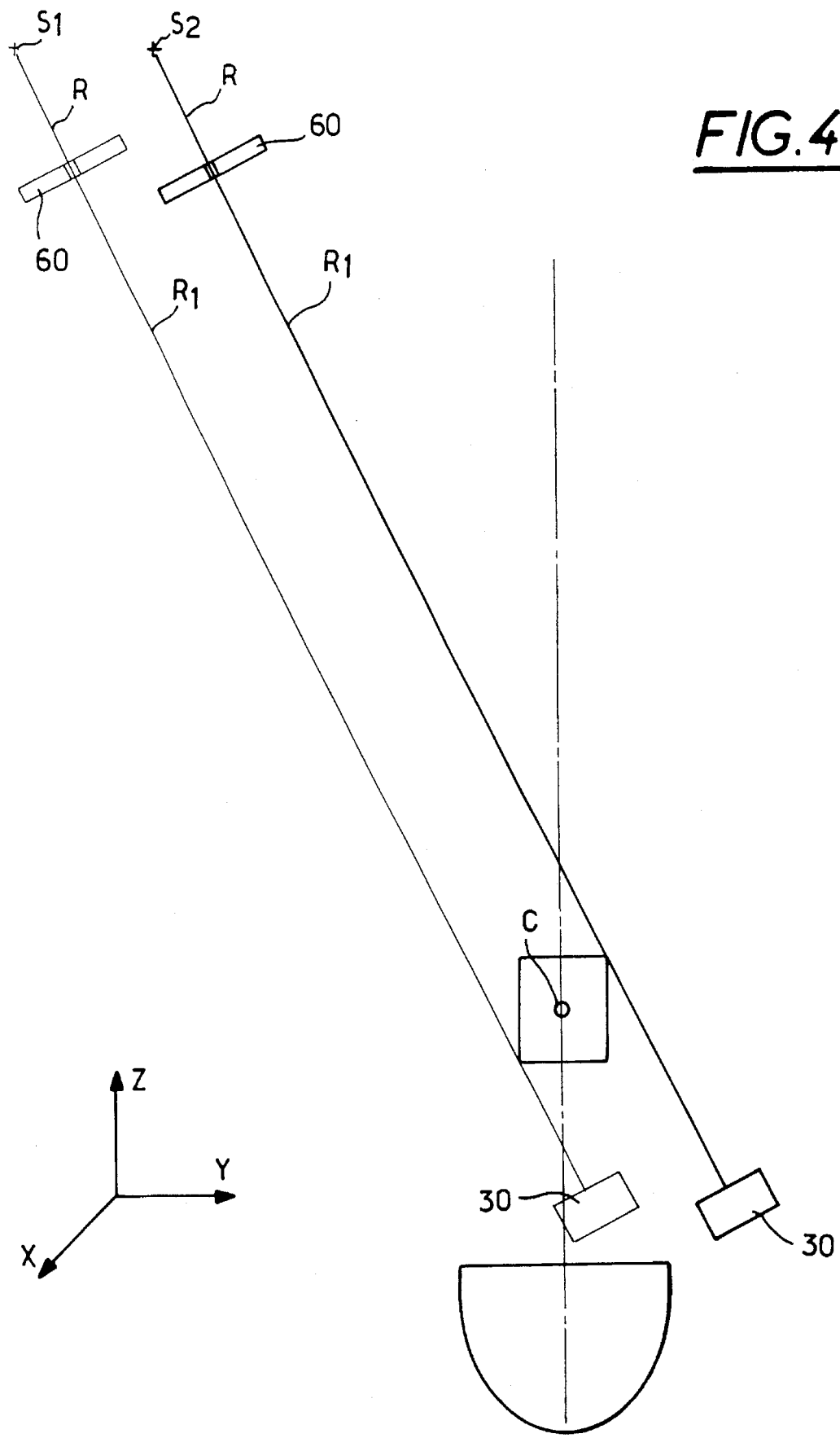
FIG. 4A represents diagrammatically the displacement between an initial position and a final position, in a simultaneous manner, of the radiation source, of the collimation device and of the radiation receiver device, according to a known displacing speed.
Figure 4B:
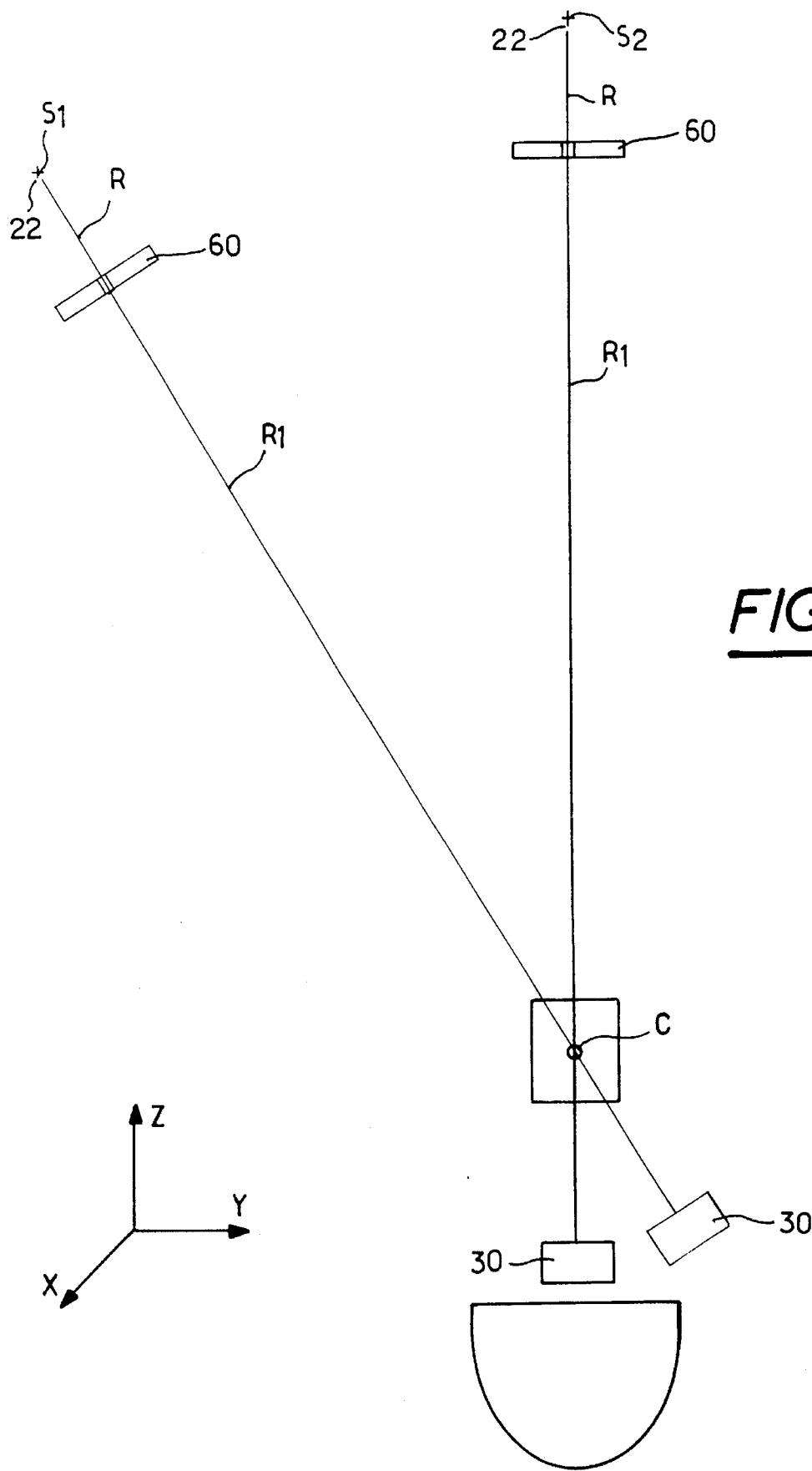
FIG. 4B represents diagrammatrically the simultaneous inclination of the radiation source, of the collimation device and of the radiation receiver device so as to form two images of said target, by pivoting around a rotation axis.

According to still another embodiment, determining means for determining the position of receiver device 30 at a given moment are foreseen to determine which is the discrete element, among the elements e1 to en, which has received the image of target C, and at which moment t, for each one of the two images resulting from two distinct angular positions $S_1, S_2$, represented on FIG. 4B of radiation source 22, as well as to determine the exact position in space of target C from the knowledge of the exact position of the two discrete elements having received two images of target C resulting from said two positions $S_1, S_2$ of radiation source 22. These determining means are preferably integrated in said calculating means 40.

According to a further particular variant embodiment, a monitor screen 50 is foreseen on which at least one image of target C obtained when displacing said receiver device 30 is projected, as well as pointing means 52 such as a computer keyboard or a mouse, well known to one skilled in the art, enabling to perform the pointing of the position of target C on screen 50 and calculating means 40 enabling to calculate the position of target C with the pointing means 52 for each image.

According to a further another embodiment, a collimation device 60 is foreseen, enabling to limit in space the radiation zone, thereby limiting the irradiation of the patient.

According to a further embodiment, means, referenced here 70, 72 are foreseen to displace simultaneously radiation source 22, optional collimation device 60 and the receiver device 30, so as to highly limit the irradiation volume and time. These displacing means advantageously perform either a displacement in translation, or in rotation, according to a direction known perpendicular to the line defined by the linear active part formed from said sensitive elements $e_1$ to $e_n$.

It is easily conceived that with the apparatuses which have just been described, an image of the zone containing the target may be obtained with a source immobile during the formation of each image, since it is foreseen displacing means of the receiver device. Thus, in such a case, only the displacement of the receiver device appears to be essential.

This is why, according to a variant embodiment, in the case where the source is immobile during the formation of each image, displacing means 70, 72 are foreseen for displacing the receiver device 30 and in synchronism the collimation device 60, so that the radiation only covers substantially the receiver device, which highly limits the irradiation volume and time.

The apparatus which has just been described in its entirety may constitute an apparatus for the treatment of a target C, preferably here by pressure waves. This target is in particular selected from the group consisting of a lithiasis, for instance a renal or biliary lithiasis; of tissues, for instance benign or malignant tumors; of bones, for instance a fracture or an osteoporosis zone.

Such an apparatus is more precisely shown on FIGS. 6 to 9 which will be described later on, with a further embodiment of the device for determining the position of a target.

The determining procedure of the position of target C results from the preceding description made with reference to FIGS. 1 to 5, and is the following:

At first, starting from position $S_1$ of source 22 shown in fantom line on FIG. 4A, position for which for instance source S1 is inclined of about 20°, with respect to the symmetry axis Z—Z, represented in dashed line, of treatment device 12, in coincidence with the displacement axis according to direction Z, a first radiation is emitted from source S1 covering target C and receiver device 30, which is for example located according to axis X, is displaced in displacement direction Y, namely perpendicular to line X-Z, advantageously according to a known translation displacement speed.

According to the preferred embodiment, as shown on FIGS. 4A, 4B and 5 where source $S_1$ is displaced simultaneously with receiver device 30, itself optionally fixedly linked with treatment device 12, and optionally with an also simultaneous displacement of collimation device 613, radiation (R) of source, here in position $S_1$, is limited ($R_1$) to the size of receiver device 30, namely to the size of bar 32 to cover the entirety of the discrete elements $e_1$ to $e_n$. The displacement distance d between the position in fantom line and the position in strong line of the treatment device, according to direction Y, is clearly visible on FIG. 4A. It is observed that source 22 is passed from position $S_1$ to position $S'_1$ by passing in front of target C. When passing in front of target C, the radiation is stopped by target C as shown in FIG. 5. It is therefore possible to detect which element, for instance here referenced $e_{C1}$, has not received the radiation emitted by source 22 in position S1 at the moment, here referenced $t_4$, which references the moment where the source is passed in front of target C for the position $S_1$, position which is noted by calculating means 40.

After this first passage, the position of source 22 may be modified to be put in the position $S_2$, with a different inclination with regard to the receiver device and target C. This position $S_2$ is for example an inclination of about 20° on the opposite side of vertical Z—Z going through target C.

At this moment, it can be performed a displacement of distance d in the reverse direction, so that, at a given moment, another discrete element of receiver device 30, for example the element referenced $e_{C2}$, does not receive the radiation from source 22 when it is stopped by target C thereby providing a second image of target C for a defined inclination of source 22, in the position $S_2$.

The datas concerning the moment of displacement, in relation to the displacement speed, as well as the position of the discrete element $e_{C2}$ not having received radiation from target C, are transmitted to the calculating means 40.

Calculating means 40 then permit to calculate the exact position of target C in a simple manner.

The practician may participate to this procedure by pointing himself, with pointing means 52, the image of target C on the screen forming means 50, which also enables the calculating means 40 to perform quickly the exact calculation of the position of target C in space relative to a reference initial position of treatment device 12. This initial position, or reference point O, may for instance be the initial position of the external focus $F_2$ or the focusing point of the pressure waves of treatment device 12.

Figure 6:
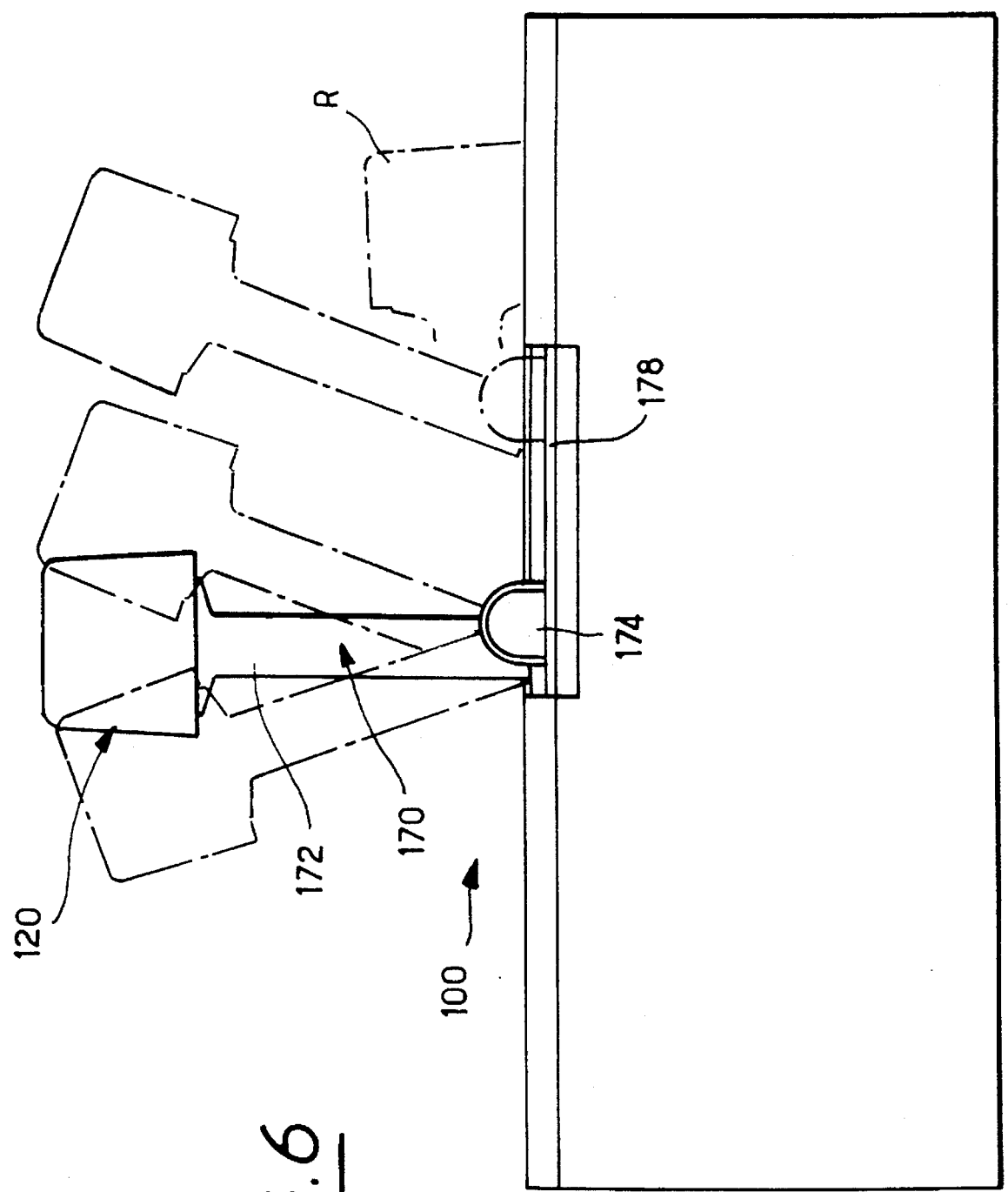
FIG. 6 represents a lateral view in diagrammatic elevation of an apparatus for the treatment of a target, equipped with a device for determining the exact position of a target, here comprising an arm in the shape of a C pivoting around an horizontal axis and displaceable in translation.

With reference to FIG. 6, it has been shown a second embodiment of an apparatus for the treatment according to the invention represented by the general reference number 100. As is usual, for all the organs fulfilling the same functions as those described with regard to the embodiments of FIGS. 1 to 5, it has been used the same reference numbers increased by 100. Thus, the pressure wave generator is referenced 112, the emitting device is reference 120 and the receiver device is referenced 130. Thus, the source itself is referenced 122. Receiver device 130 has its active part also linear and subdivided into a multiplicity of aligned discrete elements $e_1$ to $e_n$ identical to those of the preceding embodiment, and for which the first $e_1$ and the last $e_n$ have been noted in FIG. 9. In other words, the receiver device 130 has the shape of a bar 132 with a linear active part. The displacing means of bar 132 are here referenced 170 by corresponding to means 70 of simultaneous displacement foreseen in the embodiment of FIGS. 1 to 5. Displacing means 170 enable, according to an actually preferred embodiment, as shown, a displacement in translation, preferably in a direction substantially perpendicular to the sensitive active part of receiver device 132. According to another embodiment, the displacing means enable to perform a displacement in rotation according to a direction non perpendicular to the line defined by the linear active part 132.

These means 170 for the simultaneous displacement of emitting device 120 and receiver device 130 here comprise an arm in the shape of a C referenced 172 having a first end 172a supporting the emitting device 120 comprising the radiation source 122 and the collimation device 160 and a second end 172b supporting the radiation receiver device 130 integrating here the bar 132 of sensitive elements $e_1$ to $e_n$. These displacing means 170 thus constitute a common support of radiation source 122, of the collimation device 160 and of the receiver device 130.

According to an advantageous embodiment, these displacing means 170 forming a common support are mounted in rotation around a rotation axis 174 located substantially perpendicularly to the longitudinal axis of apparatus 100 as it is clearly seen on FIGS. 6 to 8. This longitudinal axis usually corresponds also to the longitudinal axis of a table 190 on which the patient to be treated is laying on. This table 190 is preferably removable, notably for enabling a full pivoting of displacing means 170 in the rest position R shown on FIG. 7 to permit to occupy a minimum volume during storage and transport.

According to another particularly advantageous embodiment, displacing means 170 forming a common support device are mounted on a translation device 176 mounted sliding by translation on guiding rails 178, mounted parallely to the longitudinal axis of the apparatus. It is understood that displacing means 170 forming a common support device, here in the shape of an arm 172 in C, are disposed laterally relative to the working table 190 aimed to receive a patient and so that the ends 172a, 172b supporting respectively the emitting device 120 and the receiver device 130, be located on opposite sides of working table 190, therefore on opposite sides of the patient and of target zone C.

The structure of the displacing means 170 constitutes an integral part of the invention and is independently patentable.

On the other hand, the invention also covers the patentably distinct conception of the emitting device 120 by foreseeing that the emitting source 122 comprises a generator element 180 emitting a radiation 182 whose initial direction is substantially perpendicular to the plane P of reception defined by the substantially linear active surface of bar 132 formed by elements $e_1$ to $e_n$ of reception of the radiation. The initially perpendicular radiation 182 is reflected into a direction of plane P by a reflecting or re-emitting device such as a cathode 184 comprising an inclined face 186 insuring this reflection or re-emission of radiation 182. The preferred radiation source is, according to the invention, a X-ray source comprising a X-ray tube whose axis is advantageously disposed substantially perpendicular to the direction of reception plane P, and whose at least a part of which is re-emitted by the reflection device, here formed by cathode 184. The collimation device 160 has a collimation slot 162 disposed parallel to plane P, and therefore also perpendicular to the initial direction of radiation 182, and whose size is foreseen to provide a radiation whose size is substantially similar to, or slightly higher than, the size of the substantially linear active part forming a bar 132 of reception device 130.

By this way, the variations of intensity of radiation reaching the active part of bar 132 are minimized, so that their effect becomes negligible on the quality of the finally obtained image, due to the substantially linear size of the bar. This bar 132 may, for example, be of about 0.6 mm with over a 230.4 mm length. By this way, the collimation device 160 produces a very thin substantially plane beam going through the patient into the direction of the bar which will minimize the amount of radiation received by the patient, which is particularly important in the preferred case of the use of X rays. On the other hand, by foreseeing the size of the slot 162 of collimation device 160 so that the width of the plane beam P at the level of the bar 132 be substantially equal to or slightly higher than that of the acquired surface of bar 132, the entirety of the radiation which goes through the patient is useful for the formation of the image.

On the other hand, due to the foreseeing of displacing means 172 forming a common support device of the emitting source 120 and of the receiver device 130 and optionally of the collimation device 160, a mechanical and undeformable link of these devices is achieved, which ensures, by an initial single setting, that the radiation is always arriving at the active part of bar 132 of the receiver device 130 irrespective of the displacement or orientation of the whole. Besides, the intensity of the radiation received will be constant, there is therefore no risk of variation of intensity of the radiation from a line to another line when scanning the zone to be imaged.

To form an image, the displacing means 170 are translated due to the translation means 176 along the patient in front of the zone to be imaged. Preferably, and as in the preceding case, concerning FIGS. 1 to 5, at least two images with two distinct inclinations of the displacing means 170 are performed, providing two different angular orientations of radiation source 120. The first orientation may, for instance, be vertical, as shown on FIGS. 6 to 8, and the second position may be inclined leftwise or rightwise from the vertical position as shown on FIG. 6, with a translated position shown in doted line, so as to form two images.

According to a particularly advantageous variant embodiment, the rotation axis 174 is disposed at half height of the zone to be imaged.

It wil be observed that with the invention it can be preset the initial position of plane P of the beam emitted by source 122 as well as that of the active part of bar 132. By this way, the displacing means forming a common support device 170, here in the shape of an arm C, 172, can be manufactured very precisely, the mounting of any bar 172 preset ends of any radiation source 122 preset to ensure a good alignment of the beam onto the linear active zone of bar 132. In this way, it can be foreseen in side ends 172a, 172b of the arm, precise setting mechanisms respectively of the position of the source, for instance by setting the position of the reflecting device 184 or of part 132 integrated with end 172b. It can also be preset the position of the collimation device 160, also integrated with end 172a of arm 172.

Once these settings performed, the positions are rigidly locked. In the case of bar 132, these can be mounted on a frame enabling a displacement in X and Y and a locking in the sought position on the end 172b of arm 172.

It is therefore clear that the invention enables, in a very simple manner, to reach all the determined technical advantages previously setforth.

The embodiments of FIGS. 1 to 9 form an integral part of the present invention and accordingly are an integral part of the present specification.

The invention also covers any feature which will appear novel over any prior art, resulting from the preceding specification or description integrating FIGS. 1 to 9.

I claim:

1. A method for determining the exact position of a target (C) relative to a reference point (O) for use in the treatment of target (C), comprising the steps of:

placing an emission device having a radiation source and a known position relative to the reference point (O) on a side of said target (C), for irradiating a zone containing said target (C);

placing, on a side of said target (C) opposite the side having said emission device, a receiver in the form of a bar comprising a linear active pan formed from a multiplicity of discrete radiation-sensitive elements defining a line, and whose positions in space are known, for receiving an image of said target (C);

simultaneously displacing said radiation source and said receiver, said displacement selected from the group consisting of a rotation according to a direction non-perpendicular to the line defined by said linear active part, and a translation relative to the line defined by said linear active part;

irradiating, for at least one displacement, said target (C) by said radiation source and receiving a resultant image of said target (C) on said receiver; and determining the position of said target (C) from said resulting image.

2. The method of claim 1, wherein said simultaneously displacing step further comprises simultaneously displacing said radiation source and said receiver in translation along a distance for emitting a radiation covering at least the target (C), said displacement being performed in translation for at least two different orientations of said radiation source and said receiver and wherein said irradiating and receiving step further comprises emitting a radiation from said radiation source for at least said two different orientations to provide at least two different images of said target on said receiver, and wherein said determining step further comprises determining the position of said target from said different images of said target.

3. The method of claim 1, wherein said simultaneously. displacing step further comprises simultaneously rotating said radiation source and said receiver about a rotation axis substantially parallel to said line defined by said linear active part, and wherein said irradiating and receiving step further comprises emitting a radiation from said radiation source for at least two different angular positions of said radiation source to provide at least two different images of said target on said receiver, and wherein said determining step further comprises determining the position of said target from said two different images of said target.

4. The method of claim 1, wherein said simultaneously displacing step further comprises mounting said radiation source and said receiver onto a common support device in the form of a C arm having one end located above said target and another end located below said target, and displacing said common support device.

5. The method of claim 4, wherein said simultaneously displacing step further comprises mounting said common support device for rotation around a rotation axis disposed substantially perpendicular to a longitudinal axis of a working table supporting a patient thereon, said rotation axis being oriented parallely to said line defined by said linear active part of said receiver.

6. The method of claim 5, wherein said simultaneously displacing step further comprises displacing said common support device in a translational direction substantially perpendicular to said longitudinal axis of said working table.

7. The method of claim 5, wherein said simultaneously displacing step further comprises displacing said common support device in a translational direction along a distance for radiating at least the target (C), said translational displacement being performed for at least two distinct orientations of said common support device obtained by rotating around said rotation axis, and wherein said irradiating step further comprises emitting a radiation for at least said two distinct orientations to provide at least two different images of the target on said receiver, and wherein said determining step further comprises determining the position of said target from said two different images of said target (C).

8. The method of claim 1, wherein said irradiating step further comprises irradiating with an X-ray source and wherein said receiving step further comprises receiving with a receiver having discrete elements sensitive to X rays.

9. The method of claim 1, wherein said irradiating step further comprises irradiating with an X-ray radiation source and wherein said receiving step further comprises receiving with a receiver having at least a fluoroscopic screen sensitive to X rays and wherein said discrete radiation-sensitive elements are sensitive to a fluoroscopic radiation emitted from said screen.

10. The method of claim 9, wherein said receiving step further comprises receiving with a receiver formed from a multiplicity of discrete solid state X-ray sensitive elements.

11. The method of claim 3, wherein said simultaneously displacing step further comprises displacing said receiver according to a predetermined known displacing speed, said method further comprising the step of determining, for each one of the two images resulting from the two distinct angular positions of the radiation source, which discrete elements in the multiplicity have received the image of target (C) and from the knowledge of the exact position of said two discrete elements, determining the exact position in space of target (C).

12. The method of claim 1, further comprising the step of providing a monitor screen on which at least one image of said target (C) obtained when displacing said receiver is projected, and providing a pointing means for pointing the position of said target (C) on the monitor screen and providing calculating means for calculating, by utilizing said pointing means, the position of said target (C) for each image.

13. The method according to claim 1, further comprising the step of providing a collimation device for limiting the space of the radiation zone.

14. A device for determining the exact position of a target (C) relative to a reference point (O) for use in the treatment of target (C), comprising:

an emission device having a radiation source and positioned in a known position relative to the reference point (O) on a side of said target (C), for irradiating a zone containing said target (C);

a receiver in the form of a bar comprising a linear active part formed from a multiplicity of discrete radiation-sensitive elements defining a line, and whose positions in space are known, said receiver being positioned on a side of said target (C) opposite the side having said emission device, for receiving a resultant image of said target (C) created by irradiation of said target by said emission device;

means for simultaneously displacing said radiation source and said receiver in a direction selected from the group consisting of a rotation according to a direction non-perpendicular to the line defined by said linear active part, and a translation relative to the line defined by said linear active part and wherein said radiation source is activated at least one time during said displacement for providing at least one image of said target to said receiver; and means for determining the position of said target (C) from said resulting image.

15. The device of claim 14, wherein the simultaneously displacing means comprises a common support device upon which the radiation source and the receiver are mounted, said common support device comprising a C arm shape having one end disposed on one side of the target and the other end disposed on another side of the target.

16. The device of claim 15, wherein the common support device is mounted for rotation around a rotation axis disposed substantially perpendicularly to a longitudinal axis of a working table supporting a patient thereon, said device emitting a radiation from said radiation source for at least two different angular positions of said radiation source to provide at least two different images of said target on said receiver.

17. The device of claim 16, wherein the common support device is mounted for translational movement relative to said longitudinal axis of said working table.

18. The device of claim 16, wherein the determining means ascertains which discrete radiation-sensitive elements in said multiplicity have received the image of target (C) for each one of two images resulting from the two distinct angular positions of the radiation source, and ascertains, utilizing the position of the receiving elements, the exact position in space of target (C).

19. The device of claim 14, further comprising a monitor screen for displaying at least one image of the target (C) obtained when displacing the receiver, a pointing means for pointing the position of target (C) on the monitor screen and, a calculating means for calculating the position of target (C) with said pointing means.

20. The device of claim 14, further comprising a collimation device for limiting the space of the radiation zone.

21. The device of claim 16, wherein the radiation source emits a radiation in an initial direction substantially perpendicular to a reception plane (P) defined by the linear active part and the rotation axis.

22. An apparatus for the treatment of a target (C) by pressure waves, comprising a determining device for determining the exact position of the target (C) relative to a reference point (O) for use in the treatment of target (C), comprising:

an emission device having a radiation source and positioned in a known position relative to the reference point (O) on a side of said target (C), for irradiating a zone containing said target (C);

a receiver in the form of a bar comprising a linear active part formed from a multiplicity of discrete radiation-sensitive elements defining a line, and whose positions in space are known, said receiver being positioned on a side of said target (C) opposite the side having said emission device, for receiving a resultant image of said target (C) created by irradiation of said target by said emission device;

means or simultaneously displacing said radiation source and said receiver according to a known displacing speed, and wherein said radiation source is activated at least one time during said displacement for providing at least one image of said target to said receiver;

calculating means for calculating the position of the receiver at a given instant from the displacing time and from the known displacing speed; and determining means for determining the position of said target from at least one image of said target.

23. The apparatus of claim 22, wherein the simultaneously displacing means comprises a common support device upon which the radiation source and the receiver are mounted, said common support device comprising a C arm shape having one end disposed on one side of the target and the other end disposed on another side of the target, the common support device being mounted for rotation around a rotation axis disposed substantially perpendicularly to a longitudinal axis of a working table supporting a patient thereon for receiving treatment of said target by said apparatus, said determining device emitting a radiation from said radiation source for at least two different angular positions of said radiation source to provide at least two different images of said target on said receiver device.

24. The apparatus of claim 23, wherein the common support device is further mounted for translational movement relative to said longitudinal axis of said working table.

25. The apparatus of claim 22, wherein the determining means ascertains which discrete radiation-sensitive elements in said multiplicity have received the image of target (C) for each one of the two images resulting from the two distinct angular positions of the radiation source and ascertaining, utilizing the position of the receiving elements, the exact position in space of target (C).

26. The apparatus of claim 22, wherein a monitor screen is provided for displaying at least one image of the target (C) obtained when displacing the receiver, and wherein a pointing means is provided for pointing the position of target (C) on the screen, and wherein said calculating means calculates the position of target (C) based on the target position pointed to by said pointing means.

27. The apparatus of claim 22, further comprising a collimation device for limiting the space of the radiation zone.

28. The apparatus of claim 23, wherein the radiation source emits a radiation in an initial direction substantially perpendicular to a reception plane (P) defined by the linear active part and the rotation axis.

29. The apparatus of claim 22, comprising a treatment device comprising a truncated ellipsoidal reflector filled with a coupling liquid comprising an internal focus immersed in said liquid, and an external focus aimed to be put into coincidence with the target to be treated, as well as at least two electrodes disposed symmetrically on opposite sides of said internal focus for generating pressure waves at said internal focus through electrical discharge in said coupling liquid.

30. The device of claim 15, wherein said simultaneously displacing means further comprises displacing said common support device according to a predetermined displacing speed, and wherein said determining means further comprises a calculating means for calculating the position of the receiver at a given instant based on the time for displacement and the predetermined displacing speed.

31. The device of claim 18, wherein said simultaneously displacing means further comprises displacing said common support device according to a predetermined displacing speed, and wherein said determining means further comprises a calculating means for calculating the position of the receiver at a given instant based on the time for displacement and the predetermined displacing speed.

32. The device of claim 21, further comprising a reflection device for reflecting the radiation in the plane (P) and in a direction perpendicular to the initial direction of the radiation.

33. A device for determining the exact position of a target (C) relative to a reference point (O) for use in the treatment of target (C), comprising:

an emission device having a radiation source and positioned in a known position relative to the reference point (O) on a side of said target (C), for irradiating a zone containing said target (C);

a receiver in the form of a bar comprising a linear active pan formed from a multiplicity of discrete radiation-sensitive elements defining a line, and whose positions in space are known, said receiver being positioned on a side of said target (C) opposite the side having said emission device, for receiving a resultant image of said target (C) created by irradiation of said target by said emission device;

means for simultaneously displacing said radiation source and said receiver according to a known displacing speed, in a direction selected from the group consisting of a rotation according to a direction non-perpendicular to the line defined by said linear active pan, and a translation relative to the line defined by said linear active part, and wherein said radiation source is activated at least one time during said displacement for providing at least one image of said target to said receiver;

calculating means for calculating the position of the receiver at a given instant from the displacing time and from the known displacing speed; and determining means for determining the position of said target from at least one image of said target.

34. The device of claim 33, wherein the simultaneously displacing means comprises a common support device upon which the radiation source and the receiver are mounted, said common support device comprising a C arm shape having one end disposed on one side of the target and the other end disposed on another side of the target.

35. The device of claim 34, wherein the common support device is mounted for rotation around a rotation axis disposed substantially perpendicularly to a longitudinal axis of a working table supporting a patient thereon, said device emitting a radiation from said radiation source for at least two different angular positions of said radiation source to provide at least two different images of said target on said receiver.

36. The device of claim 35, wherein the common support device is mounted for translational movement relative to said longitudinal axis of said working table.

37. The device according to claim 35, wherein the determining means ascertains which discrete radiation-sensitive elements in said multiplicity have received the image of target (C) for each one of two images resulting from the two distinct angular positions of the radiation source, and ascertains, utilizing the position of the receiving elements, the exact position in space of target (C).

38. The device of claim 33, further comprising a monitor screen for displaying at least one image of the target (C) obtained when displacing the receiver, a pointing means for pointing the position of target (C) on the monitor screen, and a calculating means for calculating the position of target (C) with said pointing means.

39. The device of claim 33, further comprising a collimation device for limiting the space of the radiation zone.

40. The device of claim 35, wherein the radiation source emits a radiation in an initial direction substantially perpendicular to a reception plane (P) defined by the linear active part and the rotation axis.

41. The device of claim 40, further comprising a reflection device for reflecting the radiation in the plane (P) and in a direction perpendicular to the initial direction of the radiation.

42. The device of claim 28, further comprising a reflection device for reflecting the radiation in the plane (P) and in a direction perpendicular to the initial direction of the radiation.

43. An apparatus for the treatment of a target (C) by pressure waves, comprising a determining device for determining the exact position of the target (C) relative to a reference point (O) for use in the treatment of target (C), comprising:

an emission device having a radiation source and positioned in a known position relative to the reference point (O) on a side of said target (C), for irradiating a zone containing said target (C);

a receiver in the form of a bar comprising a linear active part formed from a multiplicity of discrete radiation-sensitive elements defining a line, and whose positions in space are known, said receiver being positioned on a side of said target (C) opposite the side having said emission device, for receiving a resultant image of said target (C) created by irradiation of said target by said emission device;

means for simultaneously displacing said radiation source and said receiver in a direction selected from the group consisting of a rotation according to a direction non-perpendicular to the line defined by said linear active part, and a translation relative to the line defined by said linear active part and wherein said radiation source is activated at least one time during said displacement for providing at least one image of said target to said receiver; and determining means for determining the position of said target from at least one image of said target.

44. The device of claim 43, wherein the simultaneously displacing means comprises a common support device upon which the radiation source and the receiver are mounted, said common support device comprising a C arm shape having one end disposed on one side of the target and the other end disposed on another side of the target.

45. The device of claim 44, wherein the common support device is mounted for rotation around a rotation axis disposed substantially perpendicularly to a longitudinal axis of a working table supporting a patient thereon, said device emitting a radiation from said radiation source for at least two different angular positions of said radiation source to provide at least two different images of said target on said receiver.

46. The device of claim 45, wherein the common support device is mounted for translational movement relative to said longitudinal axis of said working table.

47. The device of claim 44, wherein the determining means ascertains which discrete radiation-sensitive elements in said multiplicity have received the image of target (C) for each one of two images resulting from the two distinct angular positions of the radiation source, and ascertains, utilizing the position of the receiving elements, the exact position in space of target (C).

48. An apparatus for the treatment of a target (C) by pressure waves, comprising a determining device for determining the exact position of the target (C) relative to a reference point (O) for use in the treatment of target (C), comprising:

an emission device having a radiation source and positioned in a known position relative to the reference point (O) on a side of said target (C), for irradiating a zone containing said target (C);

a receiver in the form of a bar comprising a linear active part formed from a multiplicity of discrete radiation-sensitive elements defining a line, and whose positions in space are known, said receiver being positioned on a side of said target (C) opposite the side having said emission device, for receiving a resultant image of said target (C) created by irradiation of said target by said emission device;

means for simultaneously displacing, according to a known displacing speed, said radiation source and said receiver in a translational direction substantially perpendicular to the line defined by said linear active part;

calculating means for calculating the position of the receiver at a given instant from the displacing time and from the known displacing speed; and determining means for determining the position of said target from at least one image of said target.

49. The apparatus of claim 48, further comprising a working table for supporting a patient thereon for receiving treatment of said target by said apparatus, said working table defining a longitudinal axis, and wherein said translational direction is substantially parallel to said longitudinal axis of said working table.

50. The apparatus of claim 49, wherein said simultaneously displacing means further comprises means for simultaneously displacing said radiation source and said receiver in a rotational direction about a rotation axis substantially parallel to the line defined by said linear active part.

51. An apparatus for the treatment of a target (C) by pressure waves, comprising a determining device for determining the exact position of the target (C) relative to a reference point (O) for use in the treatment of target (C), comprising:

an emission device having a radiation source and positioned in a known position relative to the reference point (O) on a side of said target (C), for irradiating a zone containing said target (C);

a receiver in the form of a bar comprising a linear active part formed from a multiplicity of discrete radiation-sensitive elements defining a line, and whose positions in space are known, said receiver being positioned on a side of said target (C) opposite the side having said emission device, for receiving a resultant image of said target (C) created by irradiation of said target by said emission device;

means for simultaneously displacing said radiation source and said receiver in a rotational direction about a rotation axis substantially parallel to the line defined by said linear active part; and determining means for determining the position of said target from at least one image of said target.

52. The apparatus of claim 51, further comprising a working table for supporting a patient thereon for receiving treatment of said target by said apparatus, said working table defining a longitudinal axis, and wherein said rotation axis is substantially perpendicular said longitudinal axis of said working table.

53. The apparatus of claim 52, wherein said simultaneously displacing means further comprises means for simultaneously displacing said radiation source and said receiver in a translational direction substantially perpendicular to the line defined by said linear active part.

54. The apparatus of claim 51, wherein said simultaneously displacing means further comprises means for simultaneously displacing, according to a known displacing speed, said radiation source and said receiver in a translational direction substantially perpendicular to the line defined by said linear active part.

55. The apparatus of claim 54, further comprising calculating means for calculating the position of the receiver at a given instant from the displacing time and from the known displacing speed.

* * * * *